United States Patent [19]

Hoyle et al.

[11] Patent Number: 5,451,508
[45] Date of Patent: Sep. 19, 1995

[54] METHOD AND MONOCLONAL ANTIBODIES FOR VITAMIN B12 DETERMINATION

[75] Inventors: Nicholas R. Hoyle; Gunter Pappert, both of Tutzing; Michael Grol, Feldafing; Christa Hübner-Parajsz, Tutzing, all of Germany

[73] Assignee: Boehringer Mannheim GmbH, Mannheim-Waldhof, Germany

[21] Appl. No.: 137,887

[22] Filed: Oct. 15, 1993

Related U.S. Application Data

[63] Continuation of Ser. No. 959,529, Oct. 13, 1992, abandoned, which is a continuation of Ser. No. 463,086, Jan. 10, 1990, abandoned.

[30] Foreign Application Priority Data

Jan. 11, 1989 [DE] Germany ............... 39 00 650.6

[51] Int. Cl.$^6$ ........................................ G01N 33/577
[52] U.S. Cl. ................. 435/7.93; 435/7.5; 436/532; 436/815
[58] Field of Search ............. 435/7.5, 7.93; 436/548, 436/545, 546, 505, 532

[56] References Cited

U.S. PATENT DOCUMENTS

| | | | |
|---|---|---|---|
| 3,505,019 | 4/1970 | Axen et al. | 436/545 |
| 4,423,154 | 12/1983 | Gutcho et al. | 436/545 |
| 4,950,612 | 8/1990 | Khanna et al. | 435/7.93 |
| 5,104,815 | 4/1992 | Garner et al. | 436/505 |

FOREIGN PATENT DOCUMENTS

| | | |
|---|---|---|
| 0378203 | 7/1990 | European Pat. Off. . |
| 0378204 | 7/1990 | European Pat. Off. . |
| 12826 | 12/1989 | WIPO ................... 435/7.5 |

OTHER PUBLICATIONS

Sigma Chemical Co., Techical Bulletin on Product No. V-9505, Monoclonal Anti-Vitamin B$_{12}$ Mouse Ascites Fluid Clone No. CD-29, Aug. 19, 1993.

Journal of Experimental Medicine, vol. 188, No. 1, May 1988, pp. 77-81, New York; R. Carmel et al, "Monoclonal Antibodies to Different Sites on Human Transcobalamin II (42709)".

Clin. Biochem. 18 (1965), pp. 261-266, David S. C. Lee, et al., "Human Serum Vitamin B12 Assay Methods-A Review".

Archives of Biochem. and Biophys. 153 (1972), pp. 407-409, Howard Gershman, et al., "Production and Specificity of Antibodies to B12 Derivatives".

*Primary Examiner*—Mary E. Ceperley
*Attorney, Agent, or Firm*—Felfe & Lynch

[57] ABSTRACT

For the determination of vitamin B12 a sample solution is incubated with at least two receptors $R_1$ and $R_2$ of which $R_1$ mediates the binding to the solid phase and $R_2$ is labelled, whereby a receptor is used as one of the receptors $R_1$ or $R_2$ which contains a monoclonal antibody capable of specific binding to B12 that has an affinity constant of at least $5 \times 10^9$ l/mol and a receptor is used as the other receptor $R_1$ or $R_2$ which contains B12 or an analogue thereof, the two phases are separated and the label is measured in one of the two phases.

11 Claims, 2 Drawing Sheets

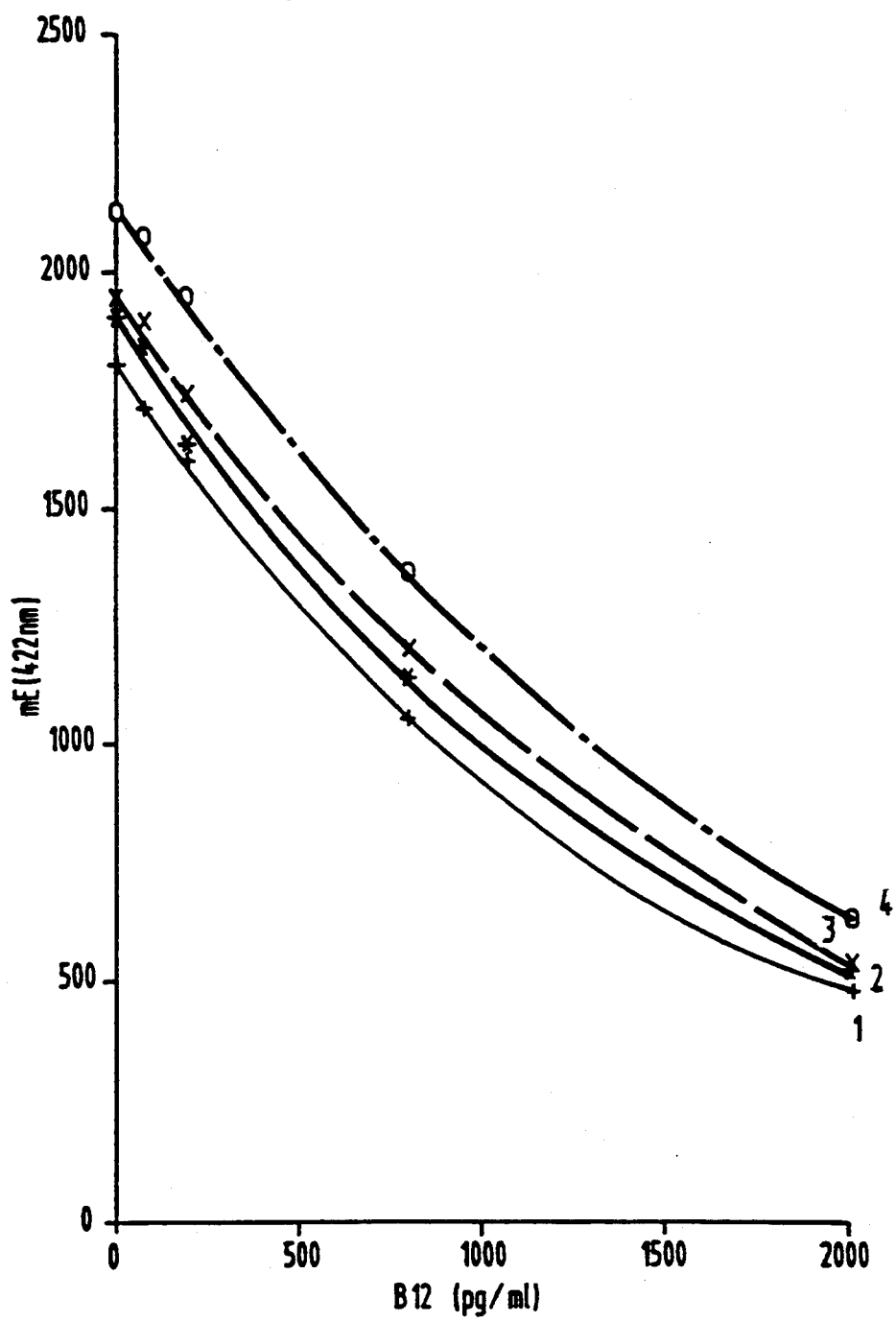

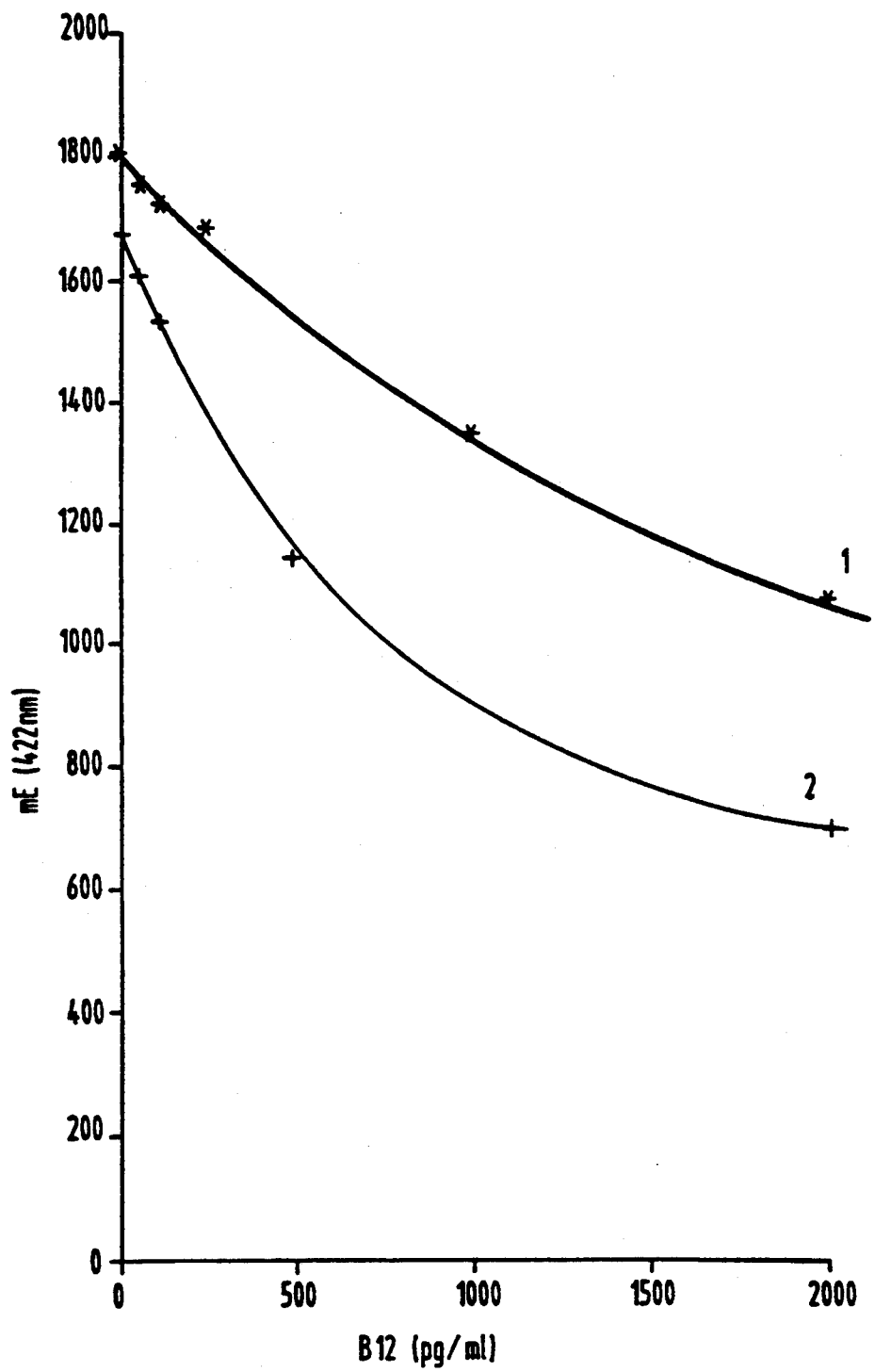

METHOD AND MONOCLONAL ANTIBODIES FOR VITAMIN B12 DETERMINATION

This application is a continuation of application Ser. No. 07/959,529, filed Oct. 13, 1992, now abandoned; which is a continuation of Ser. No. 463,086, filed Jan. 10, 1990, now abandoned.

SUMMARY OF THE INVENTION

The invention concerns determination of vitamin B12 using monoclonal antibody specific for B12 and having an affinity constant greater than $5 \times 10^9$ in a two-phase system.

DESCRIPTION

Vitamin 12 or cobalamin is an essential vitamin which is present in body fluids such as whole blood, plasma, serum in low concentrations (about $10^{-14}$ mol/l) and which has a remarkably strong binding to the B12 transport proteins (the transcobalamins). Vitamin B12 deficiency which can be caused by an inadequate vitamin intake via the food, by malabsorption syndrome, by a genetically induced deficiency of one or several transcobalamins or by the presence of gut parasites such as e.g. the fish tapeworm (diphyllobothria), can manifest itself in different symptoms which depend on the age of the individual and on the duration of the vitamin B12 insufficiency. A minor vitamin B12 deficiency causes a reduction of the red blood corpuscles whereby, in addition, a series of metabolic disorders and megaloblastic anaemias occur. In children the nervous system is affected and in some cases blindness can result.

At present the common methods for the determination of cobalamins, in particular of cyanocobalamin (vitamin B12) in very dilute aqueous solutions (such as e.g. the blood serum) are based on methods using radioactive labels in which intrinsic factor (IF) is used as the binding reagent. The common techniques use $^{57}$Co-B12 as the marker and are based on a competitive principle in which free and labelled analytes compete for binding to the IF. The separation of bound and free analyte (bound/free separation) is then effected by methods such as e.g. the use of active charcoal, IF bound to a solid phase or by magnetic separation in which IF is bound to paramagnetic particles (c.f. Brit. J. Haemat. 22 (1972) 21–31, Clin. Chem. 24 (1978) 460–466, Clin. Biochemistry 18 (1985) 261–266).

Before the determination of vitamin B12 in body fluids it is necessary to detach vitamin B12 from its binding proteins present in blood. This is carried out by heat treatment or by destruction of the binding proteins in the alkaline range (pH > 13.5) under the action of the thiol, dithiothreitol (DTT), which cleaves SH bonds (incubation of the serum sample with DTT in the alkaline range). This destruction can be intensified by adding organic substances e.g. acetone or by adding competitive cross-reactive species e.g. cobinamide. In the determination it is advantageous to add alkali cyanide to increase the extractability of vitamin B12 and to convert the cobalamins into a stable and detectable form i.e. cyanocobalamin.

The disadvantages of the known methods for the determination of vitamin B12 are in particular due to the use of intrinsic factor. Thus false results are observed when the intrinsic factor used is not sufficiently pure (max. 5 % impurity by other B12 binding proteins). Numerous samples apparently contain antibodies to IF which block the ability to bind radioactively labelled B12. This can simulate vitamin B12 values which are too low.

The object of the present invention was therefore to provide a method for the determination of vitamin B12 which does not require the use of intrinsic factor and which thus avoids the previously mentioned disadvantages and which enables an exact determination of B12 in serum in a rapid, simple and reproducible manner.

The object of the invention is therefore a method for the determination of vitamin B12 by incubation of a sample solution with at least two receptors $R_1$ and $R_2$, of which $R_1$ mediates the binding to the solid phase and $R_2$ is labelled, separation of the two phases and measurement of the label in one of the two phases, which is characterized in that a receptor is used as one of the receptors $R_1$ or $R_2$ which contains a monoclonal antibody capable of specific binding to B12 that has an affinity constant of at least $5 \times 10^9$ l/mol, and a receptor is used as the other receptor $R_1$ or $R_2$ which contains B12 or an analogue thereof.

The method according to the present invention represents a decisive advance for clinical diagnosis, since the determination of vitamin B12 was one of the last parameters for which no immunological test using immobilized monoclonal antibodies was commercially available.

In principle all current immunoassays such as radio-immunoassay, enzyme-immunoassay, fluorescence-immunoassay etc. are suitable for the immunological method of determination according to the present invention. In addition, all variants of the procedures such as competitive immunoassay, IEMA method etc. are applicable.

A competitive enzyme-immunoassay or a method according to the IEMA principle has proven to be particularly expedient for the determination of vitamin B12. In the competitive enzyme-immunoassay the B12 to be determined competes with a known amount of labelled B12 for the binding sites of the carrier-bound monoclonal antibody. The test procedure can also be carried out such that the B12 to be determined and carrier-bound B12 compete for a limited number of binding sites on the monoclonal antibody. The portion of labelled monoclonal antibody bound to the B12 fixed to the carrier is determined from the label. These variants can also be modified such that the monoclonal antibodies are used in an unlabelled form. The portion of antibody bound to the B12 fixed to the carrier is then determined by incubating with an antibody directed towards the Fc part of the antibody and determining the portion of bound label. In the IEMA method labelled monoclonal antibody is added in excess. The excess labelled antibody which is not bound to B12 is removed from the solution using a hapten-carrier matrix. The different variants of these test methods, as well as details for carrying out these procedures are described in full in the literature. Other immunological methods for the immunological determination of haptens are, however, also feasible for the determination of B12 using the antibodies according to the present invention as described for example in the German Patent Applications DE-P 38 34 766 or DE-P 38 22 750.

According to the present invention at least one monoclonal antibody is used which is directed specifically towards vitamin B12 and which has an affinity constant of $>5 \times 10^9$ l/mol preferably larger than $10^{10}$ l/mol and particularly preferably larger than $5 \times 10^{10}$ l/mol, as well as a cross-reactivity with methylcobalamin and cyanocobalamin of 100%; with cobinamide of <0.05 %; with purinylcobinamide of 1.1%; with cobyrinic acid-diamide of <0.05%; with 2-hydroxy-5,6-dimethylbenzimidazolyl-cobamide of 1.5 % and with (carboxy(2-cyanamino-4,5-dimethylphenyl)-amino)-cobamide of 0.07%.

The monoclonal antibodies can be used as complete antibodies, chimeric antibodies or bivalent antibody fragments.

Therefore, for the determination of vitamin B12, the sample solution is incubated with at least two receptors $R_1$ and $R_2$.

In this process receptor $R_1$ mediates the binding to the solid phase. For this receptor $R_1$ can either be directly bound to the solid phase or via a spacer, or else it can be present in a soluble form and not be immobilized until after the immunological reaction has been carried out. Receptor $R_1$ contains either a monoclonal antibody capable of specific binding to vitamin B12 or vitamin B12 or an analogue thereof.

The binding of the antibody or of B12 to the carrier (immobilization) is carried out according to methods familiar to the expert by adsorptive or chemical binding or by binding by a specific binding pair. In these cases one partner of the binding pair is immobilized, while the other partner is bound chemically to B12 or the antibody. The antibody or B12 can then be immobilized either before or during the immunological determination reaction by means of this binding pair. Examples of such binding pairs are biotin-streptavidin/avidin, hapten-antibody, antigen-antibody, concanavalin-antibody, sugar-lectin, hapten-binding protein.

Materials such as e.g. tubes, microtitre plates, beads or microcarriers made of plastics such as polystyrene, vinylpolymers, polypropylene, polycarbonate, polysaccharides, silicones, rubber or also treated glass (cf. e.g. E. T. Maggio, "Enzyme Immunoassay" CAC Press, Florida, 1980, in particular pages 175 to 178; EP-A-063 064; Bioengineering 16 (1974), 997–1003; C. J. Sanderson and D. V. Wilson, Immunology 20 (1971), 1061–1065) can be used as carrier materials for the immobilization of the antibody according to the present invention or for the immobilization of B12. In particular, a carrier material coated with avidin or streptavidin, in particular polystyrene, is used as the carrier material and is preferably prepared as described in EP-A 0 269 092.

Receptor $R_2$ also contains either vitamin B12 or an analogue thereof or a monoclonal antibody capable of specific binding to vitamin B12 and is labelled. The usual agents for the respective methods of determination are suitable for the labelling. Thus radioisotopes, for example $^{57}$Co, are used for the labelling in a radio-immunoassay. For an enzyme-immunoassay, all enzymes which are usually used, for example peroxidase or β-galactosidase are suitable. For a fluorescence-immunoassay the usual fluorescent groups can be used as the marker. Details of these different test methods and variants of the procedures are known to the expert. The binding of the label to B12 or to the antibody can be carried out via a specific binding pair in an analogous manner to the binding to the solid phase.

The binding of the antibody or of B12 to one of the above-mentioned binding partners is carried out by methods familiar to the expert such as via carbodiimide and hydroxysuccinimide.

When labelling B12 with an enzyme, a B12 conjugate is preferably used of the formula (I)

wherein B12 denotes the residue formed by cleavage of a —CONH$_2$ group from cyanocobalamin (vitamin B12) and R denotes a spacer, group which can be alkylene, aralkylene or arylene and wherein the spacer group can also contain one or more heteroatom. x is 0 or 1 and GP represents a marker enzyme residue containing glycosyl groups which is bound via a glycosyl residue to the —NH—N= group. In the formula (I) the —CONH— group is preferably at the d-position of the B12 residue and B12-d-CO—NH—N=GP and in particular B12-d-CO—NH—NH—CO—CH$_2$—(—O—CH$_2$—CH$_2$—)-$_3$—O—CH$_2$—CO—NH—N=GP are primarily used Peroxidase (POD) is preferably used as the enzyme marker (GP).

The B12 conjugates of the formula (I) are an object of the German Patent Application P 3900648.4 (Title: New cobalamin-acid hydrazides and cobalamin derivatives derived therefrom) by the same applicant and with the same date of application. They can be prepared by coupling (condensation) of cobalamin acid-hydrazides of the formula

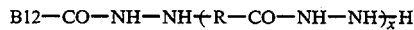

(in which B12, R and x have the meaning mentioned above), which are also an object of the above-mentioned German Patent Application P 3900648.4 which was applied for at the same time, with the OH groups of glycosyl residues of glycoproteins after they had been oxidized and the hydrazone group —NH—N=CH— glycoprotein has formed under conditions which are well-known.

In a preferred embodiment of the method according to the present invention the sample solution is prepared in the usual way in order to detach the vitamin B12 whereby the binding proteins are destroyed by addition of a thiol, dithiothreitol (DTT), in the alkaline range (pH >13.5) which can cleave SH groups or else by boiling for 30–60 minutes and subsequent centrifugation.

In the method according to the present invention for the determination of vitamin B12 the sample preparation (cleavage of the binding protein) is preferably carried out with lipoic acid (LA) or a homologue thereof of the formula (II)

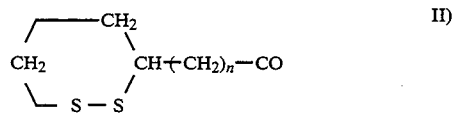

wherein n denotes 1 to 8 and in particular 3 to 5, whereby lipoic acid ( formula II, n=4) is particularly preferred.

This method is an object of the German Patent Application P 3900649.2 (Title: Method for detaching an analyte from its binding protein) by the same applicant and with the same date of application. According to this method the incubation of the sample at room temperature in the alkaline range (pH value 10 to 14; preferably using sodium hydroxide as the alkaline medium at a concentration of 0.05 to 1 mmol/l ) can be carried out in less than 15 minutes.

In this process, the acid having the formula (II) (calculated for lipoic acid with n=4) is used preferably in a range of 1 to 20 mg/ml and in particular in the range of 4 to 10 mg/ml.

The method according to the present invention yields very exact and reproducible values which is in particular due to the fact that a monoclonal antibody to vitamin B12 is used which has a very high affinity constant for vitamin B12. These antibodies are also an object of the invention. Such specific monoclonal antibodies with such high affinity constants have not been known up to now.

A further object of the invention is a method for the production of a monoclonal antibody capable of specific binding to B12 wherein inbred mice are immunized with vitamin B12-d-acid to which an immunogenic carrier material is coupled via a spacer, in particular 1-ethyl-3-(3-dimethylaminopropyl)-carbodiimide, B-lymphocytes are isolated from the immunized animals and fused with myeloma cells using transforming agents, the hybrid cells which form are cloned and cultured and the monoclonal antibodies are isolated from these cells.

For the isolation of the monoclonal antibodies according to the present invention, B12 is first linked to an immunogenic carrier material. All materials usually used for this purpose, for example, albumins such as bovine serum albumin, edestin etc. are suitable as immunogenic carrier materials. The linkage of B12 to the carrier material is carried out according to well-known methods.

Subsequently, experimental animals, for example mice, are immunized with the immunogenic conjugate. For the immunization the immunogen is, for example, administered with the adjuvant in the usual manner. Complete or incomplete Freund's adjuvant is preferably used as the adjuvant. The immunization is carried out over many months with at least four immunizations at intervals of four to six weeks (intraperitoneal injection).

B-lymphocytes are isolated from the animals which have been immunized in this way and they are fused with a permanent myeloma cell line. The fusion is carried out according to the well-known method of Köhler and Milstein (Nature 256, 1975, pages 495 to 497). The primary cultures which form during this process are cloned in the usual manner e.g. using a commercial cell sorter or by "limiting dilution". Those cultures are processed further which are positive towards B12 and show the above-mentioned cross-reactivity in a suitable test procedure such as an enzyme-immunoassay (ELISA method). In this way several hybridoma cell lines are obtained which produce the monoclonal antibodies according to the present invention. These cell lines can be cultured and the monoclonal antibodies produced by them can be isolated according to well-known methods.

In this way the antibodies used according to the present invention can be obtained, and in particular antibodies with an affinity constant of $>5\times10^9$ l/mol, preferably larger than $10^{10}$ l/mol and particularly preferably larger than $5\times10^{10}$ l/mol, as well as with a cross-reactivity with methylcobalamin and cyanocobalamin of 100 %; with cobinamide of $<0.05\%$; with purinyl-cobinamide of 1.1%; with cobyrinic acid-diamide of $<0.05\%$; with 2-hydroxy-5,6-dimethylbenzimidazolyl-cobamide of 1.5% and with (carboxy(2-cyanamino-4,5-dimethylphenyl)-amino)-cobamide of 0.07%. Antibodies which have such a high specificity are produced for example by the cell lines ECACC 88101301 and ECACC 88101302.

The cell lines are deposited at the repository ECACC (European Collection of Animal Cell Cultures, Porton Down, GB) under the respective number quoted.

The monoclonal antibodies isolated in this way are distinguished by a very high affinity (affinity constant larger than $5\times10^{-9}$) for B12 and the previously mentioned cross-reactivities. The affinity of the monoclonal antibody is preferably above $10^{10}$ l/mol and particularly preferably above $5\times10^{10}$ l/mol.

The monoclonal antibodies according to the present invention are excellently suitable for the specific determination of B12 in a sample, for example serum or plasma. For these methods of determination, the monoclonal antibodies can be used as such or as chimeric antibodies or fragments thereof which have the corresponding immunological properties, for example Fab fragments. Thus the term "monoclonal antibody" is understood to denote complete antibodies as well as the fragments.

The following Examples are intended to elucidate the invention in more detail without being limited by them. Room temperature (RT) is understood as a temperature of 25° C.±2° C. The quoted percentages refer to percentage by weight.

FIG. 1 shows a standard curve for a determination of vitamin B12 according to Example 4 with different MAB concentrations:
Curve 1: 85 ng/ml MAB
Curve 2: 90 ng/ml MAB
Curve 3: 95 ng/ml MAB
Curve 4: 100 ng/ml MAB.

FIG. 2 shows a comparison of a determination according to Example 4 (curve 2) with a determination using a polyclonal antibody (curve 1).

EXAMPLE 1

Preparation of monoclonal antibodies to vitamin B12
Preparation of the immunogen Vitamin B12-d-acid (prepared according to JACS 102 (1980) 2215) is coupled to edestin via 1-ethyl-3-(3-dimethylaminopropyl-carbodiimide (EDC).

Immunization of mice with vitamin B12 conjugate

Balb/c mice, 8 to 12 weeks old, were initially immunized intraperitoneally with 100 μg immunogen in complete Freund's adjuvant. After six weeeks, three further immunizations were carried out at intervals of 4 weeks in which 100 μg immunogen in incomplete Freund's adjuvant was administered intraperitoneally. The immunization was repeated in vitro with 100 μg immunogen 4 days, 3 days and 2 days before the fusion.

Fusion

Spleen cells from an immunized mouse were mixed with P3×63Ag8-653 myeloma cells (ATCC-CRL 8375) in a ratio of 1:5 and centrifuged (10 minutes, 300 g, 4° C.). The cells were washed once again with BSS (balanced salt solution) buffer and centrifuged at 400 g in a 50 ml conicle tube. The supernatant was discarded, the cell sediment was loosened, 1 ml PEG (MG 4000, Merck) was added and pipetted through. After one minute in a water-bath 5 ml RPMI 1640 medium (RPMI=Rosewell Parker Memory Institute) without FCS (fetal calf serum) was added dropwise over a period of 4 to 5 minutes, mixed, filled up to 50 ml with medium and subsequently centrifuged for 10 minutes at 400 g and 4° C. The sedimented cells were taken up in RPMI 1640 medium+10% FCS and $5\times10^4$ to $1\times10^5$ spleen cells or $5\times10^4$ peritoneal exudate cells were added as "feeder cel Hypoxanthine-azaserine selection medium (100 mmol/l hypoxanthine, 1 µg/ml azaserine) was added on the next day.

About 7 to 10 days after the fusion, many clones were already visible. The supernatant of the primary cultures was tested according to an ELISA method described in Example 2. Primary cultures which showed the desired cross-reaction were cloned using FACS (fluorescence activated cell sorter) in 96-well cell culture plates. $1\times10^4$ peritoneal exudate cells or $2\times10^4$ spleen cells were added per well as "feeder cells". In this manner the two hybridoma cell lines ECACC 88101301 and
ECACC 88101302 could for example be isolated and have been deposited at the repository ECACC under the cited respective repository numbers.

Induction of ascites $5\times10^6$ hybrid cells were injected i.p. once or twice in mice pre-treated with 0.5 ml Pristan. Ascites could be collected 1 to 3 weeks afterwards with an IgG concentration of 5 to 20 mg/ml. The antibodies can be isolated from this in the usual way. These monoclonal antibodies are directed specifically towards vitamin B12 and have the desired cross-reactivity. The monoclonal antibodies are denoted MAB 1 (from ECACC 88101301) or MAB 2 (from ECACC 88101302).

EXAMPLE 2

Screening test for antibodies to vitamin B12

The principle of the test used to detect the presence and specificity of antibodies to vitamin B12 in the serum of immunized mice or in the culture supernatant of the hybrid cells or in ascites is an ELISA method: microtitre plates are coated with 1 µg/ml B12 conjugate (B12-d-acid coupled to bovine serum albumin via EDC) and coating buffer (0.2 mol/l sodium carbonate/sodium bicarbonate, pH 9.3 to 9.5) at 37° C. for one hour. The plates are re-treated for 10 minutes with 0.9% sodium chloride solution and 1% albumin solution. Subsequently they are washed with 0.9% sodium chloride solution.

Afterwards they are incubated at 37° C. for one hour with 100 µl sample and washed again with 0.9% sodium chloride solution. In order to test the cross-reaction 50, 500 and 5000 µg/ml of the vitamin B12 derivative to be tested is added to the sample solution. A reduction of the measured signal in the presence of the derivative indicates a cross-reaction. A further incubation follows (1 hour, 37° C.) with 450 U/ml of a sheep-Fab-anti-mouse Fcγ peroxidase conjugate. After washing once again with 0.9% sodium chloride the peroxidase activity is determined in the usual way (for example with 2,2'azino-di-[3-ethylbenzthiazoline sulphonate (6)] (ABTS®), 30 minutes at room temperature, the difference in absorbance ΔmA is read at 422 nm).

EXAMPLE 3

Determination of the cross-reaction

The test is carried out as described in Example 2.

The antigen to be tested for cross-reaction is added in increasing concentrations (50 µg/ml, 500 µg/ml, 5000 µg/ml) to the monoclonal antibody. Afterwards the cross-reaction is calculated from the following formula:

$$\% \text{ cross-reaction} = \frac{C \text{ (vitamin B12)}}{c \text{ (cross-reacting antigen)}} \times 100$$

C=concentration of the antigen required to attain 50501% of the max. signal.

The determined values which are identical for the monoclonal antibody MAB 1 and MAB 2 are summarized in the following Table.

| cross-reacting antigen | cross-reaction |
| --- | --- |
| Methylcobalamin | 100 |
| Cyanocobalamin | 1000 |
| Cobinamide | <0.05 |
| Purinylcobinamide | 1.1 |
| Cobyrinic acid-diamide | <0.05 |
| 2-hydroxy-5,6-dimethyl-benzimidazolylcobamide | 1.5 |
| (Carboxy(2-cyanamino-4,5-dimethylphenyl)aminocobamide | 0.07 |

EXAMPLE 4

Determination of vitamin B12 a) Sample preparation

250 µl human serum are mixed with 125 µl releasing agent (consisting of 8 mg/ml lipoic acid, 1 mg/ml potassium cyanide, dissolved in 0.5 mol/l NaOH) and incubated for 15 minutes at room temperature. Afterwards 125 µl 200 mmol/l phosphate buffer, pH 4.1 is added.

b) Reagents:

Polystyrene tubes coated with thermo-BSA streptavidin (prepared according to EP-A 0269092)

Reagent 1

95 ng/ml biotinylated MAB 1 or MAB 2
(biotinylation according to JACS 100 (1978) 3585 to 3590)
40 mmol/l phosphate buffer, pH 7.2

Reagent 2

B12-d-CO—NH—NH—CO—CH$_2$—(—O—CH$_2$—CH$_2$—)$_3$—O—CH$_2$—CO—NH—N=POD (activity about 60 mU/ml)
40 mmol/l phosphate buffer, pH 7.2

Reagent 3

100 mmol/l phosphate-citrate buffer, pH 4.4
1.9 mmol/l ABT ®
3.2 mmol/l sodium perborate c) Procedure for the determination To carry out the determination 200 µl pre-treated sample and 800 µl Reagent 1 are added to a streptavidin tube and incubated for 60 minutes at room temperature. Afterwards it is washed with wash solution and 1000 µl Reagent 2 is added and incubated for 30 minutes at room temperature. It is washed with wash solution and 1000 µl Reagent 3 is added, incubated for 30 minutes at room temperature and the colour formed is measured at 422 nm as a measure of the vitamin B12 content.

d) Analogous results are obtained when instead of biotinylated complete MAB 1, biotinylated Fab fragments are used. Fab fragments are prepared as follows:

MAB 1 is cleaved with papain as described in Biochem. J. 73 (1959) 119 to 126. The Fab fragments which form in this process are separated by means of gel filtration on Sephadex G 100 and ion-exchange chromatography on DEAE cellulose according to Meth. in Enzymology 73 (1981) 418 to 459.

EXAMPLE 5

Comparison with a well-known radioimmunoassay for B12

Cyanocobalamin in 40 mmol/l phosphate buffer, pH 7.2 containing 0.9% sodium chloride, 0.9% crotein C and 0.1% potassium cyanide is used as standard. As a comparison, the test marketed by Becton Dickinson (simultaneous no boil SNB-B12/folate-radioassay) was used. In this test immobilized intrinsic factor and radioactively labelled B12 ($^{57}$Co B12) is used. Dithiothreitol (DTT) in alkaline solution is used in this test for the preparation of the samples. The correlation between this radioimmunoassay and the method according to the present invention is >0.98 in the vitamin B12 concentration range between 100 and 1400 pg/ml.

EXAMPLE 6

Vitamin B12 determination with polyclonal antibody to B12 (comparative example)

a) Collection of the antiserum 10 sheep are immunized with the immunogen described in Example 1 (0.5 ng/ml in complete Freund's adjuvant) at intervals of four weeks over 6 months. Afterwards, the antiserum is collected and purified by affinity chromatography.

b) Preparation of biotinylated Fab fragments of the polyclonal antibody to B12 (Fab-biotin)

The polyclonal antibodies are cleaved with papain as described in Biochem. J. 73 (1959) 119–126. The fragments which form in this process are separated by means of gel filtration on Sephadex G 100 and ion-exchange chromatography on DEAE cellulose according to Meth. in Enzymology 73 (1981) 418 to 459. The biotinylation is carried out as described in JACS 100 (1978) 3585–3590.

c) Procedure for the determination

The determination is carried out as described in Example 4 whereby 95 ng/ml Fab-biotin is used instead of 95 ng/ml biotinylated MAB 1.

FIG. 2 shows a comparison between a B12 determination using polyclonal and monoclonal antibodies. It can be seen that a considerably steeper calibration curve is obtained with the monoclonal antibodies according to the present invention.

It will be understood that the specification and examples are illustrative but not limitative of the present invention and that other embodiments within the spirit and scope of the invention will suggest themselves to those skilled in the art.

We claim:

1. Method for the quantitative determination of vitamin B12 in a sample consisting essentially of:
   (a) incubating said sample solution containing vitamin B12 with;
      (1) a monoclonal antibody capable of specific binding to vitamin B12, said monoclonal antibody having a specific binding constant of at least $5 \times 10^9$ l/mol for vitamin B12 as produced by hybridoma cell lines selected from the group consisting of ECACC88101301 and ECACC88101302; and
      (2) vitamin B12 or an analogue thereof, but not both, wherein the vitamin B12 or analogue thereof or the monoclonal antibody is labelled and the other mediates the binding of the vitamin B12 to a solid phase; and
   (b) separating the two phases and measuring the label in one of the two phases as a measure of the amount of vitamin B12 in said sample.

2. Method of claim 1, comprising incubating with a conjugate of biotin and the monoclonal antibody wherein a carrier material coated with streptavidin comprises the solid phase.

3. Method of claim 1, comprising incubating with a B12 conjugate of the following formula

$$B12\text{-}CO\text{-}NH\text{-}(\text{-}NH\text{-}R\text{-}CO\text{-}NH\text{-})_x\text{-}N{=}GP \quad (I)$$

wherein B12 denotes the residue formed by cleavage of a CONH$_2$ group from cyanocobalamin and R is an alkylene, aralkylene or arylene spacer group wherein said spacer group can also contain one or more heteroatoms, x is 0 or 1 and GP represents a marker enzyme residue containing glycosyl groups which is bound via a glycosyl residue to the NH—N=group.

4. Method of claim 3, comprising incubating with B12-d-CO—NH—NH—CO—CH$_2$—(—O—CH$_2$—CH$_2$—)$_3$—O—CH$_2$—CO—NH—N=GP as the B12 conjugate wherein GP is a peroxidase enzyme residue.

5. Method of claim 1 comprising
   pretreating the sample solution by addition of an acid of the formula (II):

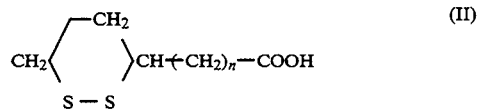

(II)

wherein n denotes a whole number from 1 to 8 before incubation with said monoclonal antibody, Vitamin B12 or analogue thereof.

6. Method of claim 5, comprising pre-treating the sample with liponic acid wherein n=4.

7. Reagent for the determination of vitamin B12 consisting essentially of:
   (a) a receptor R$_1$ which mediates the binding of the vitamin B12 to a solid phase, and
   (b) a labelled receptor R$_2$, and a detection system for the label wherein one of the two receptors R$_1$ or R$_2$ is a monoclonal antibody capable of specific binding to vitamin B12, said monoclonal antibody having a specific binding constant of at least $5 \times 10^9$ l/mol for vitamin B12 as produced by hybridoma cell lines selected from the group consisting of ECACC88101301 and ECACC88101302 and the other receptor is vitamin B12 or an analogue thereof.

8. Reagent as claimed in claim 7, comprising a matrix coated with avidin or streptavidin as the solid phase, a conjugate of biotin and the monoclonal antibody as R$_1$, a compound of the formula B12-CO—NH—(—NH—R—CO—NH—)$_x$—N=GP as R$_2$, wherein B12 denotes the residue formed by cleavage of a CONH$_2$ group from cyanocobalamin, R denotes an alkylene, aralkylene or arylene spacer group wherein said spacer group can also contain one or more heteroatoms, x is 0 or 1 and GP represents a marker enzyme residue containing glycosyl groups which is bound via a glycosyl residue to the NH—N=group and a suitable detection system for the marker enzyme.

9. Reagent of claims 7 or 8, further comprising a compound of the formula
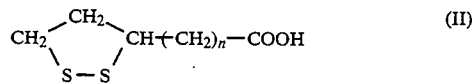
10. The reagent of claim 8 wherein $R_2$ is B12-d-CONHNHCONHNHCOCH$_2$—(O—CH$_2$—CH$_2$—)$_3$—O—CH$_2$—CO—NH—N=GP and GP is a peroxidase enzyme residue.
11. The reagent of claim 9 wherein N=4.
* * * * *

UNITED STATES PATENT AND TRADEMARK OFFICE
CERTIFICATE OF CORRECTION

PATENT NO. : 5,451,508
DATED : September 19, 1995
INVENTOR(S) : Hoyle et al

It is certified that error appears in the above-identified patent and that said Letters Patent is hereby corrected as shown below:

column 4, line 9, after "spacer" delete -- , --.

column 4, line 11, after "heteroatom", delete "." and insert therefor -- , --.

column 4, line 19, after "used" insert -- . --.

column 7, line 6, delete "cel" and insert therefor -- cells." --.

column 8, line 9, delete "50501%" and insert therefor -- 50% --.

column 8, line 50, to the end of "ABT" add -- S --.

columns 11 and 12, run the text together so that it is closed up.

Signed and Sealed this

Twenty-fifth Day of July, 2000

Attest:

Attesting Officer

Q. TODD DICKINSON

Director of Patents and Trademarks